United States Patent
Fierens et al.

(10) Patent No.: US 7,815,763 B2
(45) Date of Patent: Oct. 19, 2010

(54) POROUS MEMBRANES FOR MEDICAL IMPLANTS AND METHODS OF MANUFACTURE

(75) Inventors: Joost J. Fierens, Dworp (BE); Erhard Huesler, Bachenbülach (CH); Arik Zucker, Zürich (CH); Eric Marcoux, Erquelinnes (BE); Philippe Nicaise, Uccle (BE); Sebastien Dubois, Bois d'Haine (BE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 162 days.

(21) Appl. No.: 11/313,110

(22) Filed: Dec. 19, 2005

(65) Prior Publication Data
US 2006/0175727 A1    Aug. 10, 2006

Related U.S. Application Data

(63) Continuation-in-part of application No. 10/859,636, filed on Jun. 3, 2004, which is a continuation of application No. 09/967,789, filed on Sep. 28, 2001, now Pat. No. 6,755,856.

(60) Provisional application No. 60/637,495, filed on Dec. 20, 2004.

(51) Int. Cl.
B32B 37/15 (2006.01)
B29C 47/00 (2006.01)
A61F 2/02 (2006.01)
A61F 2/04 (2006.01)

(52) U.S. Cl. .................. 156/167; 156/244.24; 623/1.54; 623/23.76

(58) Field of Classification Search .................. 156/167, 156/172, 175, 180, 244.11, 244.24, 307.1, 156/307.7; 264/205, 308; 623/1.54, 23.76
See application file for complete search history.

(56) References Cited

U.S. PATENT DOCUMENTS

| | | | |
|---|---|---|---|
| 4,475,972 A | 10/1984 | Wong | |
| 4,580,568 A | 4/1986 | Gianturco | |
| 4,738,740 A | 4/1988 | Pinchuk et al. | |
| 4,743,252 A | 5/1988 | Martin, Jr. et al. | |
| 4,759,757 A | 7/1988 | Pinchuk | |
| 4,800,882 A | 1/1989 | Gianturco | |
| 4,907,336 A | 3/1990 | Gianturco | |
| 5,015,253 A | 5/1991 | MacGregor | |
| 5,041,126 A | 8/1991 | Gianturco | |
| 5,059,211 A | 10/1991 | Stack et al. | |

(Continued)

FOREIGN PATENT DOCUMENTS

CA    2309079    11/2004

(Continued)

OTHER PUBLICATIONS

U.S. Appl. No. 60/637,495, filed Dec. 20, 2004, Fierens et al.

(Continued)

Primary Examiner—Michael A Tolin
(74) Attorney, Agent, or Firm—Workman Nydegger (57) ABSTRACT

The present invention involves porous polymer membranes, suitable for use in medical implants, having controlled pore sizes, pore densities and mechanical properties. Methods of manufacturing such porous membranes are described in which a continuous fiber of polymer is extruded through a reciprocating extrusion head and deposited onto a substrate in a predetermined pattern. When cured, the polymeric material forms a stable, porous membrane suitable for a variety of applications, including reducing emboli release during and after stent delivery, and providing a source for release of bioactive substances to a vessel or organ and surrounding tissue.

9 Claims, 3 Drawing Sheets

U.S. PATENT DOCUMENTS

| | | |
|---|---|---|
| 5,102,417 A | 4/1992 | Palmaz |
| 5,104,404 A | 4/1992 | Wolff |
| 5,116,360 A | 5/1992 | Pinchuk et al. |
| 5,122,154 A | 6/1992 | Rhodes |
| 5,133,732 A | 7/1992 | Wiktor |
| 5,147,370 A | 9/1992 | McNamara et al. |
| 5,163,951 A | 11/1992 | Pinchuk et al. |
| 5,171,262 A | 12/1992 | MacGregor |
| 5,221,261 A | 6/1993 | Termin et al. |
| 5,282,823 A | 2/1994 | Schwartz et al. |
| 5,292,331 A | 3/1994 | Boneau |
| 5,314,444 A | 5/1994 | Gianturco |
| 5,370,683 A | 12/1994 | Fontaine |
| 5,378,239 A | 1/1995 | Termin et al. |
| 5,380,299 A | 1/1995 | Fearnot et al. |
| 5,421,955 A | 6/1995 | Lau et al. |
| 5,443,458 A | 8/1995 | Eury |
| 5,443,496 A | 8/1995 | Schwartz et al. |
| 5,449,373 A | 9/1995 | Pinchasik et al. |
| 5,476,508 A | 12/1995 | Amstrup |
| 5,496,277 A | 3/1996 | Termin et al. |
| 5,514,154 A | 5/1996 | Lau et al. |
| 5,527,354 A | 6/1996 | Fontaine et al. |
| 5,556,414 A | 9/1996 | Turi |
| 5,569,295 A | 10/1996 | Lam |
| 5,591,197 A | 1/1997 | Orth et al. |
| 5,591,224 A | 1/1997 | Schwartz et al. |
| 5,593,417 A | 1/1997 | Rhodes |
| 5,593,442 A | 1/1997 | Klein |
| 5,603,721 A | 2/1997 | Lau et al. |
| 5,609,606 A | 3/1997 | O'Boyle |
| 5,628,788 A | 5/1997 | Pinchuk |
| 5,630,829 A | 5/1997 | Lauterjung |
| 5,632,772 A | 5/1997 | Alcime et al. |
| 5,639,278 A | 6/1997 | Dereume et al. |
| 5,649,952 A | 7/1997 | Lam |
| 5,651,174 A | 7/1997 | Schwartz et al. |
| 5,653,747 A | 8/1997 | Dereume |
| 5,670,161 A | 9/1997 | Healy et al. |
| 5,674,242 A | 10/1997 | Phan et al. |
| 5,674,277 A | 10/1997 | Freitag |
| 5,693,085 A | 12/1997 | Buirge et al. |
| 5,695,516 A | 12/1997 | Fischell et al. |
| 5,697,971 A | 12/1997 | Fischell et al. |
| 5,700,285 A | 12/1997 | Myers et al. |
| 5,707,386 A | 1/1998 | Schnepp-Pesch et al. |
| 5,707,388 A | 1/1998 | Lauterjung |
| 5,709,703 A | 1/1998 | Lukic et al. |
| 5,709,713 A | 1/1998 | Evans et al. |
| 5,716,393 A | 2/1998 | Lindenburg et al. |
| 5,723,003 A | 3/1998 | Winston et al. |
| 5,723,004 A | 3/1998 | Dereume et al. |
| 5,728,158 A | 3/1998 | Lau et al. |
| 5,733,303 A | 3/1998 | Israel et al. |
| 5,735,892 A | 4/1998 | Myers et al. |
| 5,735,893 A | 4/1998 | Lau et al. |
| 5,735,897 A | 4/1998 | Buirge |
| 5,738,817 A * | 4/1998 | Danforth et al. ............ 264/603 |
| 5,741,325 A | 4/1998 | Chaikof et al. |
| 5,741,327 A | 4/1998 | Frantzen |
| 5,743,874 A | 4/1998 | Fischell et al. |
| 5,749,880 A | 5/1998 | Banas et al. |
| 5,755,771 A | 5/1998 | Penn et al. |
| 5,755,772 A | 5/1998 | Evans et al. |
| 5,755,774 A | 5/1998 | Pinchuk |
| 5,755,781 A | 5/1998 | Jayaraman |
| 5,769,884 A | 6/1998 | Solovay |
| 5,776,161 A | 7/1998 | Globerman |
| 5,776,181 A | 7/1998 | Lee et al. |
| 5,776,183 A | 7/1998 | Kanesaka et al. |
| 5,800,526 A | 9/1998 | Anderson et al. |
| 5,807,404 A | 9/1998 | Richter |
| 5,810,868 A | 9/1998 | Lashinski et al. |
| 5,810,870 A | 9/1998 | Myers et al. |
| 5,810,872 A | 9/1998 | Kanesaka et al. |
| 5,814,063 A | 9/1998 | Freitag |
| 5,817,126 A | 10/1998 | Imran |
| 5,824,037 A | 10/1998 | Fogarty et al. |
| 5,824,045 A | 10/1998 | Alt |
| 5,824,048 A | 10/1998 | Tuch |
| 5,824,054 A | 10/1998 | Khosravi et al. |
| 5,824,059 A | 10/1998 | Wijay |
| 5,827,321 A | 10/1998 | Roubin et al. |
| 5,836,964 A | 11/1998 | Richter et al. |
| 5,836,966 A | 11/1998 | St. Germain |
| 5,843,120 A | 12/1998 | Israel et al. |
| 5,843,158 A | 12/1998 | Lenker et al. |
| 5,843,161 A | 12/1998 | Solovay |
| 5,843,164 A | 12/1998 | Frantzen et al. |
| 5,846,247 A | 12/1998 | Unsworth et al. |
| 5,853,419 A | 12/1998 | Imran |
| 5,855,598 A | 1/1999 | Pinchuk |
| 5,855,600 A | 1/1999 | Alt |
| 5,860,999 A | 1/1999 | Schnepp-Pesch et al. |
| 5,861,027 A | 1/1999 | Trapp |
| 5,868,781 A | 2/1999 | Killion |
| 5,871,538 A | 2/1999 | Dereume |
| 5,876,449 A | 3/1999 | Starck et al. |
| 5,876,450 A | 3/1999 | Johlin, Jr. |
| 5,895,406 A | 4/1999 | Gray et al. |
| 5,897,589 A | 4/1999 | Cottenceau et al. |
| 5,922,021 A | 7/1999 | Jang |
| 5,928,248 A | 7/1999 | Acker |
| 5,938,682 A | 8/1999 | Hojeibane et al. |
| 5,948,018 A | 9/1999 | Dereume et al. |
| 5,954,743 A | 9/1999 | Jang |
| 5,968,091 A | 10/1999 | Pinchuk et al. |
| 5,980,552 A | 11/1999 | Pinchasik et al. |
| 5,984,965 A | 11/1999 | Knapp et al. |
| 6,017,365 A | 1/2000 | Von Oepen |
| 6,019,789 A | 2/2000 | Dinh et al. |
| 6,027,526 A | 2/2000 | Limon et al. |
| 6,033,433 A | 3/2000 | Ehr et al. |
| 6,033,434 A | 3/2000 | Borghi |
| 6,033,435 A | 3/2000 | Penn et al. |
| 6,039,756 A | 3/2000 | Jang |
| 6,048,361 A | 4/2000 | Von Oepen |
| 6,059,811 A | 5/2000 | Pinchasik et al. |
| 6,068,656 A | 5/2000 | Von Oepen |
| 6,071,308 A | 6/2000 | Ballou et al. |
| 6,086,610 A | 7/2000 | Duerig et al. |
| 6,099,561 A | 8/2000 | Alt |
| 6,106,548 A | 8/2000 | Roubin et al. |
| 6,113,627 A | 9/2000 | Jang |
| 6,117,165 A | 9/2000 | Becker |
| 6,117,535 A * | 9/2000 | Szycher et al. ............ 428/297.7 |
| 6,123,721 A | 9/2000 | Jang |
| 6,132,460 A | 10/2000 | Thompson |
| 6,165,212 A | 12/2000 | Dereume et al. |
| 6,174,326 B1 | 1/2001 | Kitakoa et al. |
| 6,179,868 B1 | 1/2001 | Burpee et al. |
| 6,190,403 B1 | 2/2001 | Fischell et al. |
| 6,193,744 B1 | 2/2001 | Ehr et al. |
| 6,193,747 B1 | 2/2001 | Von Oepen |
| 6,200,334 B1 | 3/2001 | Jang |
| 6,200,335 B1 | 3/2001 | Igaki |
| 6,203,569 B1 | 3/2001 | Wijay |
| 6,231,598 B1 | 5/2001 | Berry et al. |
| 6,231,600 B1 | 5/2001 | Zhong |
| 6,241,762 B1 | 6/2001 | Shanley |
| 6,253,443 B1 | 7/2001 | Johnson |
| 6,258,116 B1 | 7/2001 | Hojeibane |
| 6,261,318 B1 | 7/2001 | Lee et al. |
| 6,264,688 B1 | 7/2001 | Herklotz et al. |

| | | |
|---|---|---|
| 6,264,690 B1 | 7/2001 | Von Oepen |
| 6,270,524 B1 | 8/2001 | Kim |
| 6,273,913 B1 | 8/2001 | Wright et al. |
| 6,299,604 B1 | 10/2001 | Ragheb et al. |
| 6,299,635 B1 | 10/2001 | Frantzen |
| 6,325,825 B1 | 12/2001 | Kula et al. |
| 6,331,189 B1 | 12/2001 | Wolinsky et al. |
| 6,332,089 B1 | 12/2001 | Acker et al. |
| 6,340,366 B2 | 1/2002 | Wijay |
| 6,348,065 B1 | 2/2002 | Brown et al. |
| 6,377,835 B1 | 4/2002 | Schoenberg et al. |
| 6,395,020 B1 | 5/2002 | Ley et al. |
| 6,436,132 B1 | 8/2002 | Patel et al. |
| 6,451,049 B2 | 9/2002 | Vallana et al. |
| 6,485,508 B1 | 11/2002 | McGuinness |
| 6,488,702 B1 | 12/2002 | Besselink |
| 6,491,718 B1 | 12/2002 | Ahmad |
| 6,503,272 B2 | 1/2003 | Duerig et al. |
| 6,506,211 B1 | 1/2003 | Skubitz et al. |
| 6,508,834 B1 | 1/2003 | Pinchasik et al. |
| 6,540,776 B2 | 4/2003 | Sanders Millare et al. |
| 6,558,415 B2 | 5/2003 | Thompson |
| 6,572,646 B1 | 6/2003 | Boylan et al. |
| 6,589,276 B2 | 7/2003 | Pinchasik et al. |
| 6,602,285 B1 | 8/2003 | Von Oepen et al. |
| 6,607,554 B2 | 8/2003 | Dang et al. |
| 6,616,689 B1 | 9/2003 | Ainsworth et al. |
| 6,624,097 B2 * | 9/2003 | Martin et al. ............... 442/199 |
| D481,139 S | 10/2003 | Seibold et al. |
| 6,629,994 B2 | 10/2003 | Gomez et al. |
| 6,679,911 B2 | 1/2004 | Burgermeister |
| 6,682,554 B2 | 1/2004 | Oepen et al. |
| 6,723,119 B2 | 4/2004 | Pinchasik et al. |
| 6,730,252 B1 * | 5/2004 | Teoh et al. ............... 264/178 F |
| 6,740,114 B2 | 5/2004 | Burgermeister |
| 6,749,629 B1 | 6/2004 | Hong et al. |
| 6,755,856 B2 | 6/2004 | Fierens et al. |
| 6,776,794 B1 | 8/2004 | Hong et al. |
| 6,786,922 B2 | 9/2004 | Schaeffer |
| 6,790,227 B2 | 9/2004 | Burgermeister |
| 6,796,999 B2 | 9/2004 | Pinchasik |
| 6,821,292 B2 | 11/2004 | Pazienza et al. |
| 6,846,323 B2 | 1/2005 | Yip et al. |
| 6,875,228 B2 | 4/2005 | Pinchasik et al. |
| 6,881,222 B2 | 4/2005 | White et al. |
| 6,913,619 B2 | 7/2005 | Brown et al. |
| 6,916,336 B2 | 7/2005 | Patel et al. |
| 6,929,660 B1 | 8/2005 | Ainsworth et al. |
| 6,942,689 B2 | 9/2005 | Majercak |
| 6,955,686 B2 | 10/2005 | Majercak et al. |
| 6,998,060 B2 | 2/2006 | Tomonto |
| 7,029,493 B2 | 4/2006 | Majercak et al. |
| 7,060,093 B2 | 6/2006 | Dang et al. |
| 7,128,756 B2 | 10/2006 | Lowe et al. |
| 7,141,062 B1 | 11/2006 | Pinchasik et al. |
| 7,329,277 B2 | 2/2008 | Addonizio et al. |
| 7,520,892 B1 | 4/2009 | Ainsworth et al. |
| 7,625,398 B2 | 12/2009 | Clifford et al. |
| 2001/0027339 A1 | 10/2001 | Boatman et al. |
| 2001/0049549 A1 | 12/2001 | Boylan et al. |
| 2002/0019660 A1 | 2/2002 | Gianotti et al. |
| 2002/0035394 A1 | 3/2002 | Fierens et al. |
| 2002/0065549 A1 | 5/2002 | White et al. |
| 2002/0107560 A1 | 8/2002 | Richter |
| 2002/0111669 A1 | 8/2002 | Pazienza et al. |
| 2002/0151964 A1 | 10/2002 | Smith et al. |
| 2002/0169499 A1 | 11/2002 | Zilla et al. |
| 2003/0055487 A1 | 3/2003 | Calisse |
| 2003/0083736 A1 | 5/2003 | Brown et al. |
| 2003/0114918 A1 | 6/2003 | Garrison et al. |
| 2003/0120334 A1 | 6/2003 | Gerbeding |
| 2004/0051201 A1 | 3/2004 | Greenhalgh et al. |
| 2004/0093073 A1 | 5/2004 | Lowe et al. |
| 2004/0102836 A1 | 5/2004 | Fischell et al. |
| 2004/0126405 A1 | 7/2004 | Sahatjian et al. |
| 2004/0193250 A1 | 9/2004 | Von Oepen et al. |
| 2004/0230293 A1 | 11/2004 | Yip et al. |
| 2004/0236407 A1 | 11/2004 | Fierens et al. |
| 2004/0243220 A1 | 12/2004 | Gianotti et al. |
| 2005/0004650 A1 | 1/2005 | Oepen et al. |
| 2005/0004651 A1 | 1/2005 | Von Oepen et al. |
| 2005/0004655 A2 | 1/2005 | Von Oepen et al. |
| 2005/0004658 A1 | 1/2005 | Oepen et al. |
| 2005/0004659 A1 | 1/2005 | Von Oepen et al. |
| 2005/0004662 A1 | 1/2005 | Von Oepen et al. |
| 2005/0043777 A1 | 2/2005 | Von Oepen et al. |
| 2005/0043778 A1 | 2/2005 | Von Oepen et al. |
| 2005/0075716 A1 | 4/2005 | Yan |
| 2005/0222671 A1 | 10/2005 | Schaeffer et al. |
| 2006/0015173 A1 | 1/2006 | Clifford et al. |
| 2006/0106452 A1 | 5/2006 | Niermann |
| 2006/0142844 A1 | 6/2006 | Lowe et al. |
| 2006/0184232 A1 | 8/2006 | Gianotti et al. |
| 2006/0206195 A1 | 9/2006 | Calisse |
| 2006/0247759 A1 | 11/2006 | Burpee et al. |
| 2007/0021827 A1 | 1/2007 | Lowe et al. |
| 2007/0021834 A1 | 1/2007 | Young et al. |
| 2007/0135891 A1 | 6/2007 | Schneider |
| 2007/0179593 A1 | 8/2007 | Fierens et al. |
| 2007/0179601 A1 | 8/2007 | Fierens et al. |
| 2007/0213800 A1 | 9/2007 | Fierens et al. |
| 2007/0299505 A1 | 12/2007 | Gregorich et al. |
| 2008/0294239 A1 | 11/2008 | Casey |
| 2008/0294240 A1 | 11/2008 | Casey |
| 2009/0163992 A1 | 6/2009 | Osman et al. |
| 2009/0163996 A1 | 6/2009 | Bregulla |
| 2009/0163997 A1 | 6/2009 | Casey |
| 2009/0163998 A1 | 6/2009 | Casey |

FOREIGN PATENT DOCUMENTS

| | | |
|---|---|---|
| EP | 0699451 | 3/1996 |
| EP | 0709067 | 5/1996 |
| EP | 0808614 | 11/1997 |
| EP | 0928605 | 7/1999 |
| EP | 0950386 | 10/1999 |
| EP | 0983753 | 3/2000 |
| EP | 1042997 | 10/2000 |
| EP | 1095631 | 5/2001 |
| EP | 1516600 | 3/2005 |
| FR | 2774279 | 8/1999 |
| GB | 2344053 | 5/2000 |
| JP | 7-24072 | 1/1995 |
| JP | 08-206226 | 8/1996 |
| JP | 09-010318 | 1/1997 |
| JP | 10-328216 | 12/1998 |
| JP | 11-299901 | 2/1999 |
| JP | 2000312721 | 11/2000 |
| WO | WO91/17789 | 11/1991 |
| WO | WO9621404 | 7/1996 |
| WO | WO96/25124 | 8/1996 |
| WO | WO9712563 | 4/1997 |
| WO | WO9712564 | 4/1997 |
| WO | WO9714375 | 4/1997 |
| WO | WO9832412 | 7/1998 |
| WO | WO98/47447 | 10/1998 |
| WO | WO9907308 | 2/1999 |
| WO | WO99/17680 | 4/1999 |
| WO | WO9923976 | 5/1999 |
| WO | WO99/38456 | 8/1999 |
| WO | WO99/38458 | 8/1999 |
| WO | WO9939660 | 8/1999 |
| WO | WO99/49928 | 10/1999 |
| WO | WO0013611 | 3/2000 |
| WO | WO0032241 | 6/2000 |
| WO | WO0045744 | 8/2000 |

| | | |
|---|---|---|
| WO | WO00/53119 | 9/2000 |
| WO | WO0101885 | 1/2001 |
| WO | WO01/82835 | 11/2001 |
| WO | WO02/26164 | 4/2002 |
| WO | WO02064061 | 8/2002 |
| WO | WO02064065 | 8/2002 |
| WO | WO02/094127 | 11/2002 |
| WO | WO03/009779 | 2/2003 |
| WO | WO03057076 | 7/2003 |
| WO | WO2004/087015 | 10/2004 |
| WO | WO2006/055533 | 5/2006 |
| WO | WO2006066886 | 6/2006 |
| WO | WO2006/099449 | 9/2006 |
| WO | WO2008/042618 | 4/2008 |
| WO | WO2008/142566 | 11/2008 |
| WO | WO2009/046973 | 4/2009 |
| WO | WO2009/080326 | 7/2009 |
| WO | WO2009/080327 | 7/2009 |

OTHER PUBLICATIONS

U.S. Appl. No. 09/582,318, Aug. 14, 2002, Office Action.
U.S. Appl. No. 09/582,318, Mar. 7, 2003, Notice Of Allowance.
U.S. Appl. No. 09/582,318, Jul. 17, 2003, Issue Notification.
U.S. Appl. No. 09/742,144, Sep. 24, 2002, Office Action.
U.S. Appl. No. 09/742,144, May 14, 2003, Office Action.
U.S. Appl. No. 09/742,144, Aug. 29, 2003, Notice Of Allowance.
U.S. Appl. No. 09/742,144, Jan. 8, 2004, Issue Notification.
U.S. Appl. No. 09/916,394, Mar. 2, 2004, Office Action.
U.S. Appl. No. 09/916,394, Oct. 9, 2003, Office Action.
U.S. Appl. No. 09/916,394, Aug. 12, 2003, Office Action.
U.S. Appl. No. 10/884,613, Mar. 30, 2005, Office Action.
U.S. Appl. No. 10/884,613, Nov. 14, 2005, Office Action.
U.S. Appl. No. 09/967,789, Sep. 17, 2003, Office Action.
U.S. Appl. No. 09/967,789, Feb. 17, 2004, Notice Of Allowance.
U.S. Appl. No. 09/967,789, Jun. 10, 2004, Issue Notification.
U.S. Appl. No. 10/859,636, Jun. 1, 2007, Office Action.
U.S. Appl. No. 10/859,636, Dec. 31, 2007, Office Action.
U.S. Appl. No. 10/859,636, Oct. 1, 2008, Notice of Allowance.
U.S. Appl. No. 10/859,636, Apr. 15, 2008, Office Action.
U.S. Appl. No. 10/859,636, Mar. 5, 2009, Office Action.
U.S. Appl. No. 10/743,857, Mar. 15, 2007, Office Action.
U.S. Appl. No. 10/743,857, Nov. 16, 2007, Office Action.
U.S. Appl. No. 10/743,857, May 8, 2008, Office Action.
U.S. Appl. No. 10/743,857, Jan. 6, 2009, Office Action.
U.S. Appl. No. 10/743,857, May 27, 2009, Office Action.
U.S. Appl. No. 10/903,013, Mar. 15, 2007, Office Action.
U.S. Appl. No. 10/903,013, Nov. 19, 2007, Office Action.
U.S. Appl. No. 10/903,013, May 14, 2008, Office Action.
U.S. Appl. No. 10/903,013, Jan. 5, 2009, Office Action.
U.S. Appl. No. 10/903,013, May 27, 2009, Office Action.
U.S. Appl. No. 10/903,014, Mar. 15, 2007, Office Action.
U.S. Appl. No. 10/903,014, Nov. 16, 2007, Office Action.
U.S. Appl. No. 10/903,014, May 13, 2008, Office Action.
U.S. Appl. No. 10/903,014, Jan. 13, 2009, Office Action.
U.S. Appl. No. 10/903,014, Jun. 1, 2009, Office Action.
U.S. Appl. No. 10/903,080, Mar. 15, 2007, Office Action.
U.S. Appl. No. 10/903,080, Nov. 19, 2007, Office Action.
U.S. Appl. No. 10/903,080, May 12, 2008, Office Action.
U.S. Appl. No. 10/903,080, Dec. 30, 2008, Office Action.
U.S. Appl. No. 10/903,080, May 27, 2009, Office Action.
U.S. Appl. No. 10/909,117, Aug. 22, 2007, Office Action.
U.S. Appl. No. 10/909,117, May 12, 2008, Office Action.
U.S. Appl. No. 10/909,117, Dec. 30, 2008, Office Action.
U.S. Appl. No. 10/909,117, May 27, 2009, Office Action.
U.S. Appl. No. 10/909,118, Mar. 29, 2007, Office Action.
U.S. Appl. No. 10/909,118, Nov. 19, 2007, Office Action.
U.S. Appl. No. 10/909,118, May 12, 2008, Office Action.
U.S. Appl. No. 10/909,118, Jan. 5, 2009, Office Action.
U.S. Appl. No. 10/954,948, Mar. 15, 2007, Office Action.
U.S. Appl. No. 10/954,948, Nov. 16, 2007, Office Action.
U.S. Appl. No. 10/954,948, May 15, 2008, Office Action.
U.S. Appl. No. 10/954,948, Jan. 13, 2009, Office Action.
U.S. Appl. No. 10/954,948, May 29, 2009, Office Action.
U.S. Appl. No. 10/955,425, Mar. 15, 2007, Office Action.
U.S. Appl. No. 10/955,425, Nov. 16, 2007, Office Action.
U.S. Appl. No. 10/955,425, May 13, 2008, Office Action.
U.S. Appl. No. 10/955,425, Jan. 13, 2009, Office Action.
U.S. Appl. No. 10/955,425, May 28, 2009, Office Action.
U.S. Appl. No. 11/404,450, Feb. 4, 2009, Office Action.
U.S. Appl. No. 11/404,450, Mar. 17, 2009, Office Action.
U.S. Appl. No. 11/601,475, Jul. 22, 2008, Office Action.
U.S. Appl. No. 11/601,475, Jan. 6, 2009, Office Action.
U.S. Appl. No. 11/601,475, Jun. 1, 2009, Office Action.
U.S. Appl. No. 10/859,636, filed Oct. 19, 2009, Notice of Allowance.
U.S. Appl. No. 10/903,080, filed Jan. 13, 2010, Notice of Allowance.
U.S. Appl. No. 10/909,117, filed Jan. 13, 2010, Notice of Allowance.
U.S. Appl. No. 10/909,118, filed Jul. 24, 2009, Office Action.
U.S. Appl. No. 10/909,118, filed Jan. 13, 2010, Notice of Allowance.
U.S. Appl. No. 10/954,948, filed Jan. 13, 2010, Notice of Allowance.
U.S. Appl. No. 11/404,450, filed Sep. 30, 2009, Office Action.
U.S. Appl. No. 11/601,475, filed Jan. 15, 2010, Notice of Allowance.
U.S. Appl. No. 11/732,244, filed Sep. 28, 2009, Office Action.
U.S. Appl. No. 12/608,335, filed Oct. 29, 2009, Calisse.
U.S. Appl. No. 10/241,523, filed Aug. 18, 2004, Office Action.
U.S. Appl. No. 10/241,523, filed Oct. 25, 2004, Office Action.
U.S. Appl. No. 10/241,523, filed Mar. 8, 2005, Office Action.
U.S. Appl. No. 10/241,523, filed Jun. 3, 2005, Office Action.
U.S. Appl. No. 10/241,523, filed Aug. 23, 2005, Office Action.
U.S. Appl. No. 10/241,523, filed Nov. 16, 2005, Office Action.
U.S. Appl. No. 10/241,523, filed Apr. 27, 2006, Office Action.
U.S. Appl. No. 10/743,857, filed Feb. 12, 2010, Notice of Allowance.
U.S. Appl. No. 10/859,636, filed Feb. 1, 2010, Notice of Allowance.
U.S. Appl. No. 10/903,013, filed Feb. 12, 2010, Notice of Allowance.
U.S. Appl. No. 10/903,014, filed Feb. 5, 2010, Notice of Allowance.
U.S. Appl. No. 10/955,425, filed Feb. 26, 2010, Notice of Allowance.
U.S. Appl. No. 11/404,450, filed Apr. 22, 2010, Office Action.
U.S. Appl. No. 11/435,260, filed Jan. 10, 2008, Office Action.
U.S. Appl. No. 11/435,260, filed Mar. 26, 2008, Office Action.
U.S. Appl. No. 11/435,260, filed Dec. 16, 2008, Office Action.
U.S. Appl. No. 11/435,260, filed Jun. 18, 2009, Office Action.
U.S. Appl. No. 11/435,260, filed Jun. 26, 2009, Office Action.
U.S. Appl. No. 11/731,820, filed Jan. 27, 2010, Office Action.
U.S. Appl. No. 11/731,882, filed Feb. 3, 2010, Office Action.
U.S. Appl. No. 11/732,244, filed May 5, 2010, Notice of Allowance.
U.S. Appl. No. 11/805,584, filed Apr. 27, 2009, Office Action.
U.S. Appl. No. 11/805,584, filed Oct. 29, 2009, Office Action.
U.S. Appl. No. 11/805,584, filed Mar. 15, 2010, Office Action.
U.S. Appl. No. 11/961,290, filed May 6, 2009, Office Action.
U.S. Appl. No. 11/961,290, filed Dec. 18, 2009, Office Action.
U.S. Appl. No. 11/961,384, filed May 26, 2009, Office Action.
U.S. Appl. No. 11/961,384, filed Oct. 8, 2009, Office Action.
U.S. Appl. No. 11/961,754, filed Jul. 22, 2009, Office Action.
U.S. Appl. No.11/961,754, filed Apr. 5, 2010, Notice of Allowance.
U.S. Appl. No. 11/973,707, filed Jun. 9, 2009, Office Action.
U.S. Appl. No. 11/973,707, filed Mar. 19, 2010, Office Action.
U.S. Appl. No. 11/961,775, filed Oct. 1, 2009, Office Action.
U.S. Appl. No. 11/961,775, filed Mar. 31, 2010, Office Action.
U.S. Appl. No. 10/743,857, filed Jun. 25, 2010, Notice of Allowance.
U.S. Appl. No. 10/859,636, filed May 19, 2010, Notice of Allowance.
U.S. Appl. No. 10/903,013, filed Jun. 24, 2010, Notice of Allowance.
U.S. Appl. No. 10/903,014, filed May 26, 2010, Office Action
U.S. Appl. No. 10/903,014, filed Jun. 24, 2010, Notice of Allowance.
U.S. Appl. No. 10/955,425, filed Jun. 25, 2010, Notice of Allowance.
U.S. Appl. No. 11/732,244, filed Jun. 21, 2010, Notice of Allowance.
U.S. Appl. No. 10/743,857, filed Aug. 18, 2010, Issue Notification.
U.S. Appl. No. 10/903,013, filed Aug. 18, 2010, Issue Notification.
U.S. Appl. No. 10/954,948, filed Jul. 6, 2010, Notice of Allowance.
U.S. Appl. No. 11/601,475, filed Jul. 9, 2010, Notice of Allowance.
U.S. Appl. No. 11/731,820, filed Aug. 5, 2010, Notice of Allowance.
U.S. Appl. No. 11/961,754, filed Jul. 28, 2010, Notice of Allowance.

* cited by examiner

POROUS MEMBRANES FOR MEDICAL IMPLANTS AND METHODS OF MANUFACTURE

REFERENCE TO RELATED APPLICATIONS

The present application is a continuation-in-part of U.S. patent application Ser. No. 10/859,636, filed Jun. 3, 2004, which is a continuation of U.S. patent application Ser. No. 09/967,789, filed Sep. 28, 2001. This application also claims the benefit of priority from U.S. provisional patent application Ser. No. 60/637,495, filed Dec. 20, 2004.

FIELD OF THE INVENTION

The present invention relates to porous membranes suitable for covering medical implants such as stents for intravascular delivery, implants covered with such membranes and methods for making the porous membranes.

BACKGROUND OF THE INVENTION

Covered stents for implantation into a body vessel, duct or lumen generally include a stent and a cover attached to the stent. A porous structure of the cover, depending on the porosity, may enhance tissue ingrowth after the covered stent has been implanted. A porous structure affixed to an implantable device also may serve as a reservoir for bioactive components and/or reduce embolization by trapping thrombus against a vessel wall.

Porous membranes for use in medical devices are known in the art. For example, U.S. Pat. No. 4,759,757 to Pinchuk describes the formation of a porous membrane by leaching water soluble inorganic salts incorporated into the membrane to create pores where the salt crystals were initially located. U.S. Pat. No. 6,540,776 to Sanders Millare et al. describes a perforated membrane in which a pattern of interstices is created by removing material, for example, by laser cutting. The foregoing manufacturing methods require at least two process steps to form a porous membrane.

One step processes for forming porous membranes also are known in the art, for example, using spinning techniques. U.S. Patent Application Publication No. 20040051201 to Greenhalgh et al. describes an electrospinning process in which a membrane is formed from a plurality of randomly-oriented, intertangled, non-woven fibrils.

Spinning techniques that produce less random, but non-uniform membranes, also are known. For example, U.S. Pat. No. 4,475,972 to Wong describes a porous polymeric material made by a process in which polymeric fibers are wound on a mandrel in multiple overlying layers. The fibers contain unevaporated solvent when deposited in contact with one another, so that upon evaporation of the solvent the fibers bond together. The fibers laid in one traverse are wound on the mandrel parallel to each other and at an angle with respect to the axis of the mandrel. In the next traverse, the angle of winding is reverse to the previous angle, so that the fibers crisscross each other in multiple layers to form the porous structure.

U.S. Pat. No. 4,738,740 to Pinchuk et al. describes a spinning method similar to that of Wong and further comprising intermittently applying a electrostatic charge to ensure reattachment of broken fibers to the mandrel. U.S. Pat. No. 5,653,747 to Dereume describes a vascular graft with an expandable coating produced by the spinning technique of Wong and having pores that open when the tubular support member expands.

All of the foregoing spinning processes suffer from an inability to tightly control the pore size and pore pattern of the resulting membranes. More specifically, lateral deviation of the fibers using previously known spinning techniques has resulted in unsteady collocation of the fibers and the need to deposit multiple layers to ensure adequate coverage. Consequently, previously-known techniques produce either stiff membranes formed of multiple layers and unsatisfactory porosity, or porous, elastic membranes with insufficient strength.

In view of the foregoing, it would be desirable to provide membranes having controlled porosity, pore pattern and pore distribution.

It further would be desirable to provide a one step manufacturing process to produce membranes having controlled porosity, pore pattern and pore distribution.

It still further would be desirable to provide a one step manufacturing process to produce membranes having controlled porosity and/or pore pattern wherein the membrane includes a bioactive substance that may be eluted from the membrane after implantation.

It also would be desirable to provide manufacturing processes to produce membranes having the desired porosity, pattern and distribution characteristics for use in medical implants.

SUMMARY OF THE INVENTION

In view of the foregoing, it is an object of the present invention to provide membranes for use in medical implants having controlled porosity, pore pattern and pore distribution.

It is another object of this invention to provide a one step manufacturing process to produce membranes having controlled porosity, pore pattern and pore distribution.

It is a further object of the present invention to provide a one step manufacturing process to produce membranes having controlled porosity and/or pore pattern wherein the membrane includes a bioactive substance that may be eluted from the membrane after implantation.

It is also an object of this invention to provide manufacturing processes to produce membranes having the desired porosity, pattern and distribution characteristics for use in medical implants.

These and other objects of the present invention are accomplished by providing a membrane comprising a plurality of fibers that are deposited onto a substrate with a predetermined and reproducible pattern. The substrate may be either a mandrel or a surface of an implantable device, such as a stent. In a preferred embodiment, the fibers comprise a polymer that is sufficiently elastic and robust that the membrane follows the movements of the stent from loading onto a stent delivery system to deployment and implantation, without adversely affecting the performance of the membrane of the stent.

In a preferred embodiment, the membrane is formed using a computer-controller substrate that moves in a precisely controlled and reproducible manner. The polymer used to form the fibers, e.g., a polyurethane or a copolymer thereof, is dissolved in a solvent and extruded through one or more extrusion heads onto a moving substrate. By moving the extrusion head back and forth with a specific velocity along the axis of the substrate, specific filament angles or patterns may be deposited. In accordance with one aspect of the present invention, the number of passes, substrate shape and motion and extrusion head speed and material flow are controlled to provide a predetermined fiber diameter that is deposited to produce desired membrane properties, such as pore size and density.

The membrane may either be fixed on the exterior surface of an implantable device, such as a stent, on the interior surface or both. Where an exterior covering is desired, the membrane may be directly deposited on the implantable device. Alternatively, the covering may be deposited on a mandrel to form a separate component, and then affixed to the implantable device in a later manufacturing step.

In accordance with another aspect of the present invention, the membrane may comprise composite fibers having a viscous sheath co-extruded around a solid core component, or alternatively may comprise co-extruded viscous components. In this manner, a membrane may be created wherein the individual fibers are loaded with a desired bioactive agent, such as a drug, that elutes from the matrix of the membrane without resulting in substantial degradation of the mechanical properties of the membrane.

Methods of manufacturing covered implantable medical devices including the porous membranes of the present invention also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention generally relates to medical implants, such as stents, having a porous membrane and the methods of making such membranes and medical implants. In accordance with the present invention, polymer membranes are provided that have well-defined pores based on a controlled deposition of fibers onto a substrate. In this manner a permeable membrane having a predetermined pore size and distribution may be obtained.

Acute as well as late embolization are a significant threat during and after intravascular interventions such as stenting in saphenous vein grafts (SVG) and carotid arteries, where released particles can lead to major cardiac attacks or strokes, respectively. Covered stents for treatment of atherosclerotic lesions constructed according to the present invention comprise a porous membrane bonded to an exterior surface, and interior surface, or both, of a stent. Advantageously, the covered stent of the present invention may serve both to reduce embolization during an interventional procedure and prevent late embolization by tethering emboli and particles to the vessel wall.

The inventive membrane may be engineered to provide any of a number of design properties, including: single and multi-component material composition; loading of one or more physiological (bioactive) substances into the polymer matrix; predetermined isotropic or an-isotropic mechanical properties; and predetermined pore geometry.

In accordance with the principles of the present invention, polymeric material is deposited onto a computer-controlled movable substrate. Controlling the relative location and motion of the material source with regard to the deposition location on the substrate and process parameters, such as material flow and viscosity of the deposited material, permits generation of a multitude of different patterns for the membrane.

The porous membrane of the present invention is sufficiently strong and flexible for use in medical devices, and preferably comprises steps of extruding a continuous fiber-forming biocompatible polymeric material through a reciprocating extrusion head onto a substrate to form an elongated fiber. The fiber is deposited on the substrate in a predetermined pattern in traces having a width of from 5 to 500 micrometers, adjacent traces being spaced apart from each other a distance of between 0 and 500 micrometers.

Preferably, the fibers have a predetermined viscous creep that allows adjacent traces to bond to one another at predetermined contact points upon deposition. The number of overlapping or crossing fibers generally should be less than 5, preferably less than 4, and most preferably 1 or 2. When cured, the biocompatible material provides a stable, porous membrane.

Figure 1:
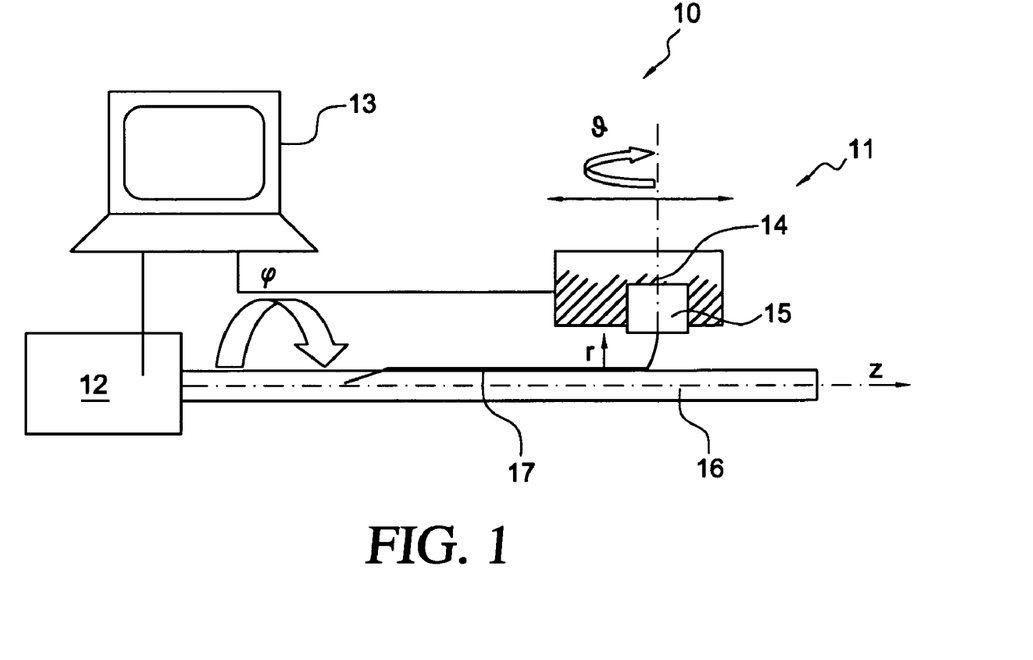
FIG. 1 is a schematic depiction of a membrane manufacturing system constructed in accordance with the principles of the present invention.

Referring to FIG. 1, apparatus 10 suitable for forming the porous membranes of the present invention comprises polymer extrusion machine 11 coupled to numerically controlled positioning system 12. Computer 13 controls the flow of extrudate 14 through extrusion head 15 as well as relative motion of extrusion head 15 and substrate 16 resulting from actuation of positioning system 12.

Apparatus 10 permits highly-localized deposition of the extrudate with four degrees of freedom onto a substrate to form a membrane. The degrees of freedom are: z—the longitudinal motion of substrate 16 relative to extrusion head 15; φ—the angular movement of substrate 16 relative to extrusion head 15; r—the distance between extrusion head 15 and substrate 16; and θ—the pivotal angle of extrusion head 15. The polymer strands 17 may be deposited onto the substrate under computer control to form any of the patterns described herein below.

In a preferred embodiment, the substrate comprises a rotating mandrel. Polymer is extruded through reciprocating extrusion head 15 representing the first degree of freedom z, and with a controlled distance between the extrusion head and substrate 16, representing the second degree of freedom r. Preferably, the distance between the extrusion head and substrate is between 0 to 50 mm, and more preferably between 0.5 and 20 mm. As the polymer is deposited onto the substrate, the substrate is rotated through a predetermined angle φ, corresponding to the third degree of freedom. In this manner, fibers 17 extruded from extrusion head 15 form a two-dimensional membrane on substrate 16. In addition, by pivoting the extrusion head along its vertical axis, fourth degree of freedom θ may be employed, thus making it possible to deposit more than one filament simultaneously while maintaining a set inter-fiber distance.

The four degrees of freedom discussed above may be independently controlled and if needed, synchronized, to attain a spatial resolution of material deposition having an order of magnitude of microns or higher. Optionally, the second degree of freedom r may be fixed if stable polymer deposition has been achieved. The fourth degree of freedom is not required when extruding only one filament.

Extrusion head 15 may have one or more outlets to deposit an extruded polymer fiber onto substrate 16 in traces having an inter-trace distance ranging between 0 to 1000 micrometers. The width of the individual trace (corresponding to the fiber width) may vary between 5 to 500 micrometers, and more preferably is in the range of 10 to 200 micrometers. Pore size is a function of trace width and inter-trace distance and may be selected by selection of these variables from between 0 (i.e., a tight covering) to 200 micrometers (i.e., to form a filter or tether to trap emboli against a vessel wall). Due to the precise control of fiber deposition, it is possible to create a membrane with desired porosity, strength and flexibility with a very small number of overlapping traces or crossing traces. The number of overlapping or crossing traces in the membrane of the present invention generally should be less than 5, preferably less than 4, and most preferably 1 to 2.

The biocompatible polymer is liquefied either by dissolving the biocompatible material in solvents or by thermally melting the biocompatible material, or both. The viscosity of the liquefied material determines the viscous creep properties and thus final pore size and inter-pore distance when the material is deposited on the substrate. Preferably, the viscous creep is controlled so that desired geometrical and physical properties are met upon deposition. By controlling the viscosity and amount of the deposited material on the substrate and consequently the viscous creep of the polymer before curing, the specified inter-pore distance, pore width and inter-fiber bonding may be achieved. Alternatively, the substrate may be heated to facilitate relaxation and/or curing of the trace width after deposition on the substrate.

Viscosity also may be controlled by adjustment of the distance r of extrusion head 15 relative to substrate 16, the concentration of the solvent in extrudate 14 and/or the heating temperature, ambient pressure, and extrusion parameters. With the viscous creep of the fibers being appropriately controlled, the traces deposited on the substrate will bond to one another at predetermined contact points upon deposition.

A specified pore size of the membrane may be achieved by, but is not limited to, lateral deposition distance between two adjacent material traces, extrusion parameters, and/or extrusion head outlet diameters and extrusion pressure. The latter two parameters also affect the fiber diameter, thus in combination with the fiber deposition pattern selected, permit selection and control of the mechanical properties of the membrane.

Suitable biocompatible materials include but are not limited to polyurethane and copolymers thereof, silicone polyurethane copolymer, polypropylene and copolymers thereof, polyamides, polyethylenes, PET, PEEK, ETFE, CTFE, PTFE and copolymers thereof. Preferred materials for forming membranes of the present invention are polyurethane and copolymers thereof. The polymers may in addition include any biologically active substance having desired release kinetics upon implantation into a patient's body.

Figure 2A:
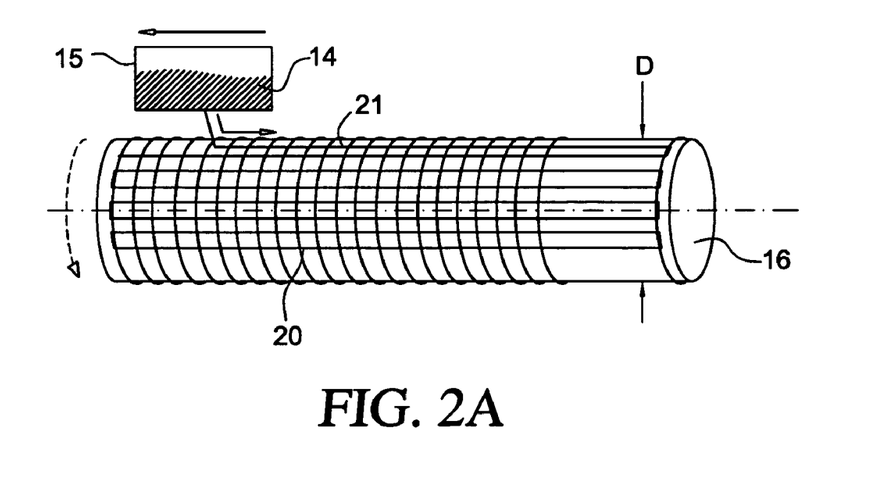
FIGS. 2A-2C are perspective views depicting exemplary patterns for depositing fibers onto a moving substrate in accordance with the present invention.
Figure 2B:
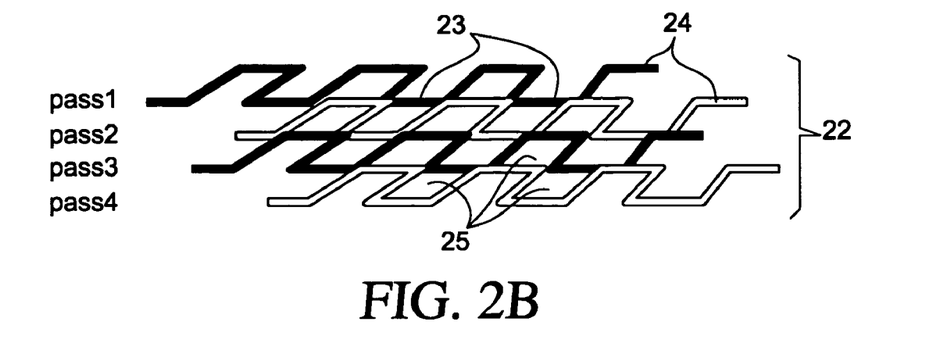
Figure 2C:
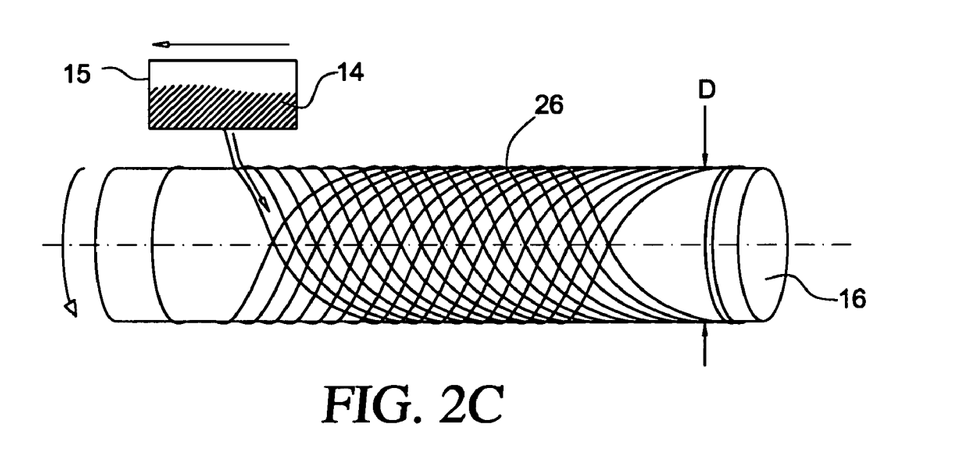

Referring now to FIGS. 2A to 2C, exemplary patterns formed by apparatus 10 during deposition of the fibers from extrusion head 15 of the present invention are described. In FIG. 2A, membrane 20 is formed on substrate 16 having diameter D by reciprocating extrusion head 15 longitudinally relative to the longitudinal axis of the substrate, followed by indexed angular movement of the substrate while the extrusion head is held stationary at the ends of the substrate. In this manner, traces 21 having a controlled width and inter-trace spacing may be deposited on the substrate.

Once the longitudinal fibers have been deposited on the substrate, the substrate is rotated 360° while the extrusion head is indexed along the length of the substrate, thereby forming a regular pattern of square or rectangular pores having a predetermined size. Alternatively, if extrusion head 15 is provided with multiple outlets, multiple parallel fibers may be deposited in a single longitudinal pass.

FIG. 2B illustrates alternative membrane pattern 22, wherein the substrate is rotated through precise angular motions during longitudinal translation of the extrusion head. Instead of depositing a straight longitudinal strand, as in the pattern of FIG. 2A, the pattern of FIG. 2B includes a series of "jogs" 23 in each longitudinal filament 24. When adjacent filaments 24 are deposited on the substrate, the contacting portions of the traces bond to one another to define pores 25 having a predetermined size. In this manner, with each longitudinal pass of the extrusion head, a line of pores 25 of predetermined size in formed in a single layer membrane.

FIG. 2C shows another pattern 26 by which the membrane of the present invention may be built up. In this embodiment, positioning system 12 employs two degrees of freedom, z and φ, simultaneously, resulting in a "braid-like" structure. Preferably the extruded fibers retain a high unevaporated solvent content when deposited on substrate 16, so that the fibers fuse to form a unitary structure having a predetermined pore size.

More generally, apparatus 10 may be used to deposit one or more traces of a biocompatible material on substrate 16 while extrusion head 15 is reciprocated along the length of the substrate. An extrusion head having multiple outlets permit the deposition of multiple filaments on the substrate during a single translation of the extrusion head or rotation of the substrate. All translational and rotational motions of the components of apparatus 10 are individually or synchronously controlled by computer 13, thus permitting the membrane to be configured with any desired pattern.

As discussed above with respect to FIGS. 2A-2C, apparatus 10 permits fibers to be deposited with any of a number of possible alternative patterns. By depositing the fibers first in multiple passes longitudinal passes followed by indexed translation of the extrusion head and simultaneous rotation of the substrate, as in FIG. 2A, two trace layers may be generated that cross or overlap to form a membrane having a regular grid of pores. In this case, only one degree of freedom is used at any one time. Alternatively, addressing two degrees of freedom alternatingly, as in the pattern of FIG. 2B, a series of "jogs" may be introduced into the individual fibers. In this case, the traces do not cross but only contact each other, thereby creating a line of pores in a single layer membrane. Still further, by addressing two degrees of freedom simultaneously, a braided structure such as depicted in FIG. 2C may be obtained, in which a specified pore size and shape is attained by varying the distance between two parallel traces of material.

In accordance with one aspect of the present invention, extrusion is performed with chemically or thermally liquefied material, or both. The viscosity of the extrudate may be controlled by the concentration of the solvent, by enhancing evaporation of the solvent from the deposited material trace by means of heating the substrate, by varying the distance r between the extrusion head and the substrate, or by adjusting the extrusion temperature of the material so that a well-defined viscous creep of the material occurs after deposition onto the substrate.

Adjustment of the viscous creep allows fusion of the traces at contact points and thus formation of a two-dimensional membrane having desired mechanical strength characteristics. By appropriately setting these parameters accurate material deposition may be achieved with reduced lateral aberrations of the filaments compared to previously-known membrane manufacturing techniques.

As will of course be understood, the diameter of the substrate should be selected based upon the dimensions of the medical implant or stent to which the membrane is to be affixed. For example, the diameter may be selected based upon the expanded configuration of the medical implant or stent. The implant to be covered may be balloon-expandable or self-expandable. In a preferred embodiment, the implant is a self-expandable stent comprising a superelastic material such as a nickel-titanium alloy.

Figure 3:
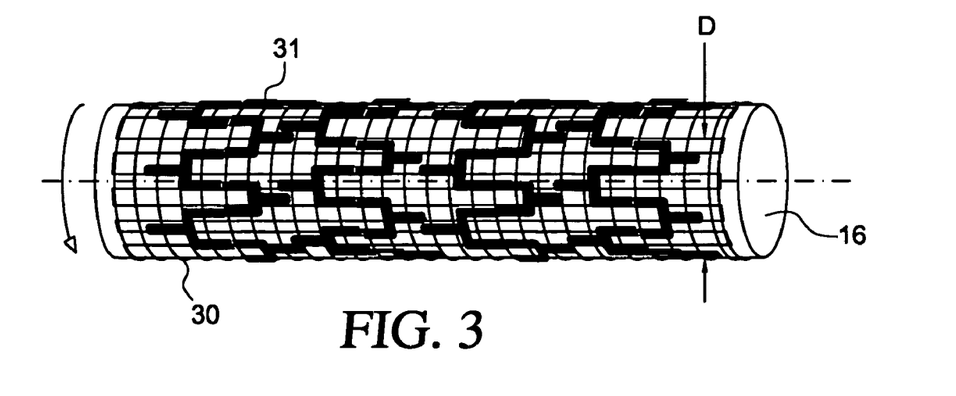
FIG. 3 is a perspective view illustrating a stent covered with the membrane of the present invention.

Referring to FIG. 3, stent 30 covered with membrane 31 of the present invention is described. Stent 30 may comprise any suitable design, such as a plastically deformable slotted tube or self-expanding superelastic structure. Porous membrane 31 may be deposited directly onto the medical implant, such as stent 30 which is employed as the substrate during the membrane deposition process.

Alternatively, the membrane may be deposited on a mandrel and after curing may be bonded in a separate step to the medical implant. In the latter case, thermal drying and/or evaporation of the solvent cures the biocompatible material while on the substrate. Once the membrane has cured sufficiently so that the mechanical properties of the membrane permit it to be removed from the substrate, the membrane may be bonded to a surface of the implant using a solvent, adhesive or thermal technique. In this case, the surface of the implant may be pre-processed to optimize bonding, for example by activation of the surface, coating of the surface with liquified polymer or other appropriate treatments of the surface.

Figure 4:
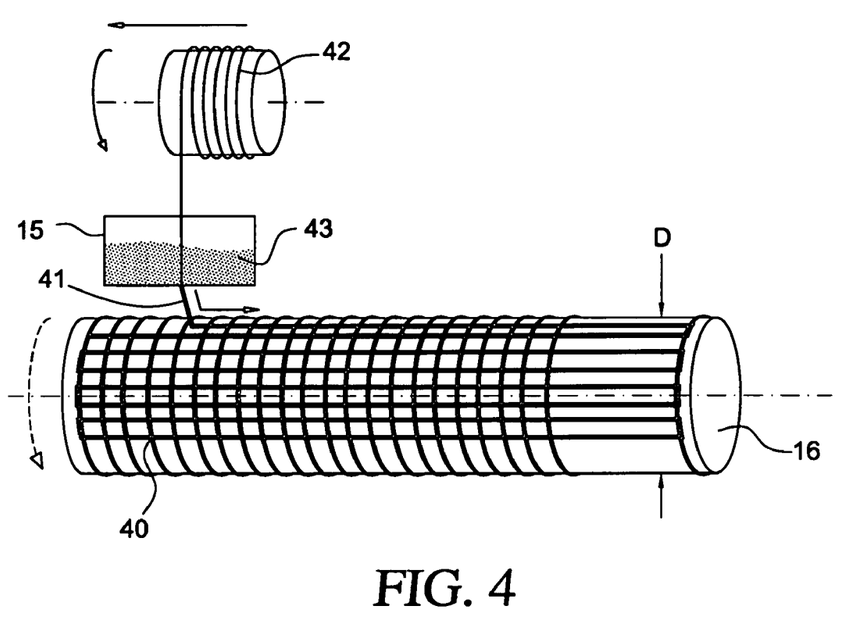
FIG. 4 is a schematic depiction of a membrane manufacturing process wherein the fibers comprise a core filament having a polymeric sheath.

Referring now to FIG. 4, an alternative method of forming a porous membrane, suitable for use in a medical implant, is described. In this embodiment, membrane 40 comprises multi-component fiber 41 including core filament 42 coated with at least second biocompatible material 43 having the same or different chemical, physical, mechanical, biocompatible and or biologically active properties. Material 43 may incorporate one or more biologically active substances that elute into the patient's bloodstream after the medical implant is implanted.

Multi-component fiber 41 may be deposited onto the substrate to form a two-dimensional contiguous structure. The individual components of fiber 41 may be selected to provide different characteristics to the membrane, which may employ any of the pattern designs discussed herein above. For example, core filament 42 may provide mechanical stability, while material 43 may serve as and interface to the biological environment, enhance the adhesive properties for inter-trace bonding and/or enhance bonding of the membrane to the medical implant.

Suitable materials for the core filament include but are not limited to polyamides, polyethylenes, PET, PEEK, ETFE, CTFE, and PTFE and copolymers thereof, and metal wire or fiber glass. Suitable materials for ensheathing core filament 41 include but are not limited to polyurethane and copolymers thereof, silicone polyurethane copolymer, polypropylene and copolymers thereof, polyamides, polyethylenes, PET, PEEK, ETFE, CTFE, PTFE and copolymers thereof.

Figure 5:
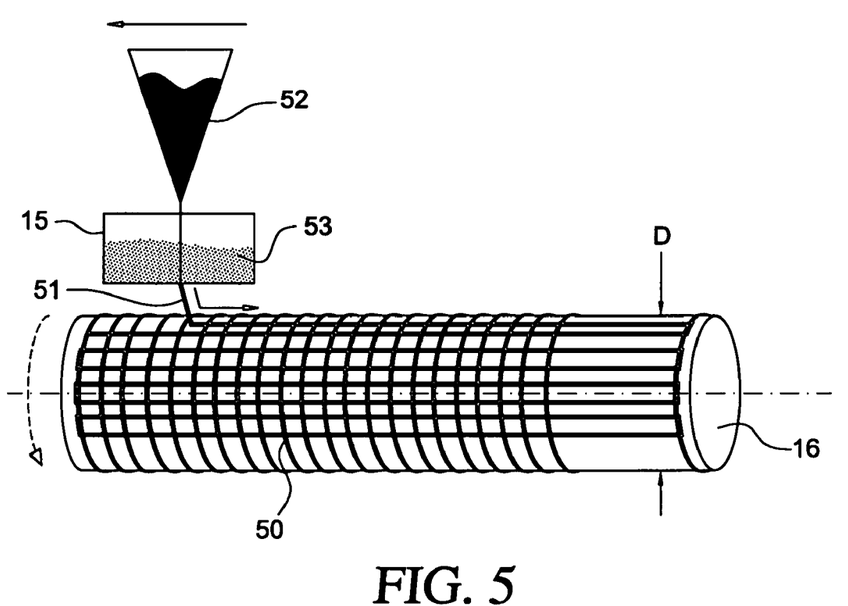
FIG. 5 is a schematic depiction of a membrane manufacturing process wherein the fibers comprise a coextrusion of two polymers.

Referring to FIG. 5, a further alternative method of forming the porous membrane of the present invention is described. In the method depicted in FIG. 5, membrane 50 comprises co-extruded fibers 51 formed of at least first biocompatible material 52 and second biocompatible material 53. Materials 52 and 53 may have the same or different chemical, physical, mechanical, biocompatible and or physiologically active properties. Fibers 51, while illustrated as being co-axially co-extruded, alternatively may be co-extruded co-linearly.

Suitable materials for first material 52 include but are not limited to polyamides, polyethylenes, PET, PEEK, ETFE, CTFE, PTFE and copolymers thereof. Suitable materials for second material 53 include but are not limited to polyurethane and copolymers thereof, silicone polyurethane copolymer, polypropylene and copolymers thereof, polyamides, polyethylenes, PET, PEEK, ETFE, CTFE, PTFE and copolymers thereof.

It should be understood that the present invention is not limited to membranes for use on stents. Rather, the membranes of the present invention may be affixed to any other medical device or implant that is brought into an intracorporal lumen for limited or extended implant durations. Such devices include vascular protection devices to filter emboli that are only transiently introduced into the body. Further applications for such porous membranes may be devices configured to be introduced into other body lumens or ducts, such as the trachea, esophagus, and biliary or urinary lumina.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method of making a single-layer porous membrane for use in medical implants comprising:
   extruding a continuous fiber-forming biocompatible polymeric material through a reciprocating extrusion head to form an elongated fiber;
   depositing the fiber with a width of 5 to 500 micrometers onto a substrate in a predetermined pattern of non-crossing traces, the traces extending adjacently from a first end to a second end of the substrate, each trace contacting its adjacent traces in an alternating manner, the traces defining a plurality of pores of predetermined sizes, the fiber having a predetermined viscous characteristic that enables adjacent traces to bond to each other; and
   thermally drying the biocompatible material on the substrate to provide a stable, single-layer porous membrane.

2. The method of claim 1 wherein depositing the fiber comprises depositing the fiber to form a single-layer porous membrane having a thickness equal to the thickness of the fiber.

3. The method of claim 2 wherein depositing the fiber comprises defining pores having an essentially square shape.

4. The method of claim 1 wherein depositing the fiber comprises depositing the fiber with a high unevaporated solvent content to facilitate bonding between adjacent fibers.

5. The method of claim 1, wherein the substrate comprises a vascular implant.

6. The method of claim 5 wherein the vascular implant is a stent.

7. The method of claim 1 wherein extruding a continuous fiber-forming biocompatible polymeric material comprises extrusion coating a polymeric sheath surrounding a solid core filament.

8. The method of claim 1 wherein extruding a continuous fiber-forming biocompatible polymeric material comprises extrusion coating a first polymeric sheath surrounding a second polymeric core filament.

9. The method of claim 1 further comprising removing the porous membrane from the substrate and affixing the porous membrane to a surface of a medical implant.

* * * * *